United States Patent [19]

Rhodes et al.

[11] Patent Number: 4,672,130

[45] Date of Patent: Jun. 9, 1987

[54] PROCESS OF MAKING XENORHABDIN ANTIBIOTICS

[75] Inventors: Stuart H. Rhodes; Graham R. Lyons; Richard P. Gregson, all of New South Wales; Raymond J. Akhurst, Tasmania; Michael J. Lacey, Campbell, all of Australia

[73] Assignee: Commonwealth Scientific and Industrial Research Organisation and Biotechnology Australia Pty. Ltd., Australia

[21] Appl. No.: 819,894

[22] Filed: Jan. 16, 1986

Related U.S. Application Data

[63] Continuation of Ser. No. 623,969, Jun. 25, 1984, abandoned.

[30] Foreign Application Priority Data

Oct. 26, 1982 [AU] Australia ................................ PF6503

[51] Int. Cl.$^4$ ............................................. C12P 17/18
[52] U.S. Cl. ................................................... 348/453
[58] Field of Search ................................ 548/453, 452

[56] References Cited

PUBLICATIONS

Merck Index (10th Edition), p. 127.

*Primary Examiner*—Christopher Henderson
*Attorney, Agent, or Firm*—Welsh & Katz, Ltd.

[57] ABSTRACT

The new 1,2-dithiolo[4,3-b]pyrrole derivatives (also designated as Xenorhabdins) are antibiotics and pesticides. Their bio-syntheses from Xenorhabdus nemtophilus or X. luminescens, and the pharmaceutical and pesticidal formulations containing them have been disclosed. Several xanthydrol and acetate derivates of Xenorhabdins have been prepared.

8 Claims, 1 Drawing Figure

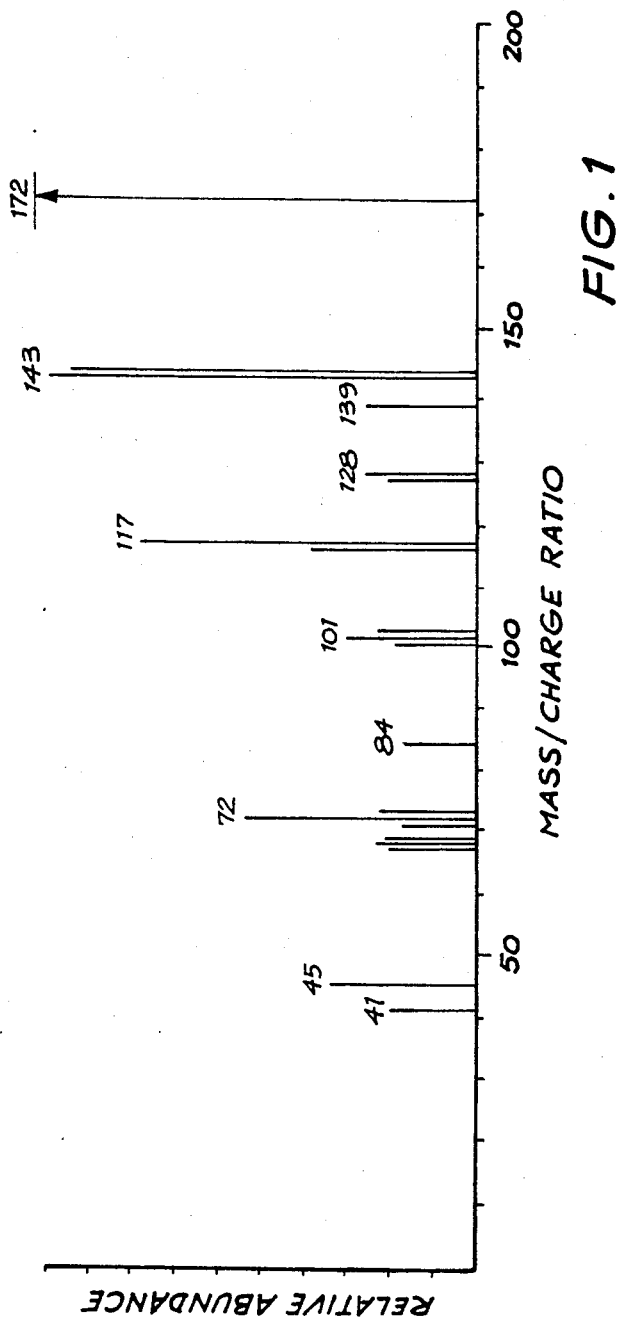

PROCESS OF MAKING XENORHABDIN ANTIBIOTICS

This is a continuation of application Ser. No. 623,969, filed June 25, 1984, now abandoned.

TECHNICAL FIELD

This invention relates to antibiotic and pesticides, and in particular to antibiotic substances and pesticides which may be isolated from micro-organisms associated with certain nemotades.

BACKGROUND ART

Insect pathogenic nematodes of the families Heterorhabitidae and Steinernematidae are known to be symbiotically associated with bacteria of the genus Xenorhabdus, and it has been observed that these bacteria have the ability to inhibit the activity of other bacterial genera. Xenorhabdus are described by Thomas and Poinar, Int J. Syst. Bacteriol., 29 (4), 352–360, (1979),Akhurst, Int. J. Syst. Bacteriol., 33 (1), 38–45, (1983), Akhurst, J. Gen. Microbiol., 121, 303–309, (1980), and Akhurst, J. Gen. Microbiol., 128, 3061–3065, (1982). The activity is believed to derive from antibiotic substances released by the Xenorhabdi. Paul et al. (J. Chem. Ecol, 7 (3), 589–594 (1981), for example, have confirmed the presence of certain indoles and stilbenes in cultures of X. nematophilus and X. luminescens, and have shown that these compounds are active against a number of non-pathogenic, bioluminescent bacteria.

Paul et al. suggest that several antibacterial mechanisms may be operating in the Xenorhabdus systems. This possibility could explain the fact that we have succeeded in isolating from X. nematophilus, antibiotic compounds of quite different structure from those investigated by Paul et al. The new compounds have, moreover, proven to be active against a wide range of bacteria, including Gram positive species and are also effective as pesticides, especially as insecticides.

Bacteria of the genus Xenorhabdus are found to occur in two forms, called primary (1°) and secondary (2°) form. The two forms of Xenorhabdus can be differentiated most easily by their colonial morphology. Antibiotic activity is exhibited by primary form bacteria, but not by secondary forms.

DISCLOSURE OF THE INVENTION

Some of the compounds of this invention, which were isolated from primary form *X. nematophilus* strain T319 (Enterobacteriaceae), are characterized in that they yield a peak due to ions of elemental composition $C_5H_4N_2OS_2$ in their 70 eV electron ionisation mass spectra, and that the collision-induced dissociation spectrum ('Collision Spectroscopy', Plenum Press, New York 1978, Ed., R. G. Cooks) of these ions is that depicted in FIG. 1. The collision-induced dissociation spectrum may be obtained by scanning a VG Micromass 70/70 mass spectrometer at a constant ratio of the magnetic field to electric sector voltage, with helium in its collision cell at an estimated pressure of 0.04 Pa.

The compounds of the invention exhibit antibiotic and pesticidal activity. Some of the compounds are 1,2-dithiolo[4,3-b]pyrrole derivatives, whilst others are as yet unidentified. Compounds of the invention are either isolated from *X. nematophilus* or *X. luminescens*, or derived from compounds so isolated.

The 1,2-dithiolo[4,3-b]pyrrole derivatives may be represented by the general formula:

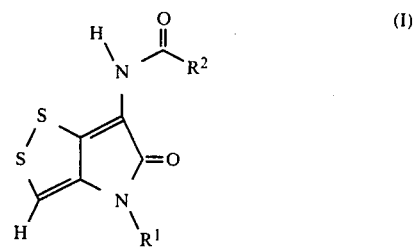

These compounds of the invention have been called "xenorhabdins". The xenorhabdins isolated from *X. nematophilus* are as follows:

| | |
|---|---|
| Xenorhabdin I   | $R^1 = H$, $R_2 = $ n-pentyl |
| Xenorhabdin II  | $R^1 = H$, $R_2 = $ 4-methylpentyl |
| Xenorhabdin III | $R^1 = H$, $R_2 = $ n-heptyl |
| Xenorhabdin IV  | $R^1 = CH_3$, $R_2 = $ n-pentyl |
| Xenorhabdin V   | $R^1 = CH_3$, $R_2 = $ 4-methylpentyl |

Salts, acyl and other derivatives of the xenorhabdins and other compounds of the invention also form part of the present invention.

Thus the xenorhabdin compounds of the invention are 6 -hexanoylamino-1,2-dithiolo[4,3-b]pyrrol-5-(4H)-one, 6-(5-methyl-hexanoylamino)-1,2-dithiolo[4,3-b]pyrrol-5-(4H)-one, 6-octanoylamino-1,2-dithiolo[4,3-b]pyrrol-5(4H)-one, 6-hexanoylamino-4-methyl-1,2-dithiolo[4,3-b]pyrrol-5(4H)-one and, 6-(5-methylhexanoylamino)-4-methyl-1,2-dithiolo[4,3-b]pyrrol-5(4H)-one.

The invention also includes processes for the preparation of the aforesaid antibiotic and pesticidal compounds, which, inter alia, may be isolated from a natural source, such as cultures of Xenorhabdus, in a manner known per se, for example by extraction with an organic solvent such as ethanol, DMSO, ethyl acetate or chloroform, and subsequent chromatorgraphy, preferably with a silica gel stationary phase.

Thus the invention also provides a process for the production of xenorhabdins I, II, III, IV or V, which process comprises culturing a xenorhabdin producing strain of *Xenorhabdus nematophilus* or *Xenorhabdus luminescens* in a suitable culture medium and separating the xenorhabdin I, II, III, IV or V from the resultant culture broth.

Also included within the invention is a process for the production of other compounds having antibiotic and/or pesticidal activity, which process comprises culturing a xenorhabdin producing strain of *Xenorhabdus nematophilus* or *Xenorhabdus luminiscens* in a suitable culture medium and separating the other compounds having antibiotic and/or pesticidal activity from the resultant culture broth.

In a further aspect, the invention provides a continuous process for the production of xenorhabdins I, II, III, IV or V, which process comprises culturing a xenorhabdin producing strain of *Xenorhabdus nematophilus* or *Xenorhabdus luminescens* in a suitable culture medium in a fermenter in the presence of oxygen, controlling the temperature and pH of the culture in said fermenter, continuously adding fresh culture medium to said fermenter and continuously collecting culture from said fermenter at such a rate to maintain the volume of culture in said fermenter within selected limits, and separating xenorhabdins I, II, III, IV and V from the collected culture.

The invention also provides a continuous process for the production of other compounds having antibiotic and/or pesticidal activity, which process comprises culturing a xenorhabdin producing strain of *Xenorhabdus nematophilus* or *Xenorhabdus luminescens* in a suitable culture medium in a fermenter in the presence of oxygen, controlling the temperature and pH of the culture in said fermenter, continuously adding fresh culture medium to said fermenter and continuously collecting culture from said fermenter at such a rate to maintain the volume of culture in said fermenter within selected limits, and separating the other compounds having antibiotic and/or pesticidal activity from the collected culture.

In yet another aspect, the invention also provides pharmaceutical formulations which comprise at least one compound of formula I supra or other compound of the invention having antibiotic activity, together with a pharmaceutically acceptable carrier or diluent therefor.

Also included within the scope of the invention are pesticidal formulations which comprises at least one compound of formula I supra or other compound of the invention having pesticidal activity, together with a carrier or diluent therefor.

The invention also provides a method for the prevention or control of infectious disease in a mammal requiring said prevention or control, which method comprises administering to said mammal an effective amount of at least one compound of formula I supra or other compound of the invention having antibiotic activity, or of a formulation containing same.

The invention further provides a method of killing or controlling pests at a locus at which said pests occur or are expected to occur which method comprises applying to said locus an effective amount of at least one compound of formula I supra or other compound of the invention having pesticidal activity, or of a formulation containing same.

MODES FOR CARRYING OUT THE INVENTION

Suitable culture media include materials containing suitable carbon and energy sources, such as glucose or other sugars, glycerol, or lipids, suitable nitrogen sorces such as ammonia, urea, amino acids, peptides or proteins, appropriate quantities or inorganic nutrients such as phosphate, potassium, magnesium, calcium and trace elements, and some source of vitamins and growth factors, e.g. yeast extract.

Such a medium used and found suitable for production of xenorhabdins in batch culture is the following yeast extract-salts (YS) broth: yeast extract $5gL^{-1}$; $(NH_4)_2SO_4 5gL^{-1}$; $MgSO_4.7H_2O$, $0.2gL^{-1}$; $KH_2PO_4 0.5gL^{-1}$ and $K_2HPO_4 0.5gL^{-1}$, pH 6.8.

Such a medium used and found suitable for production of xenorhabdins in continuous culture is the following: glycerol $20gL^{-1}$; yeast Extract $10gL^{-1}$; $(NH_4)_2SO_4 20gL^{-1}$; $KH_2PO_4 10gL^{-1}$; $MgSO_4.7H_2O 2.5gL^{-1}$; $CaCl_2.2H_2O 0.29gL^{-1}$; $FeSO_4.7H_2O 27.8mgL^{-1}$; $MnSO_4.H_2O 8.45mgL^{-1}$; $ZnSO_4.7H_2O 14.4mgL^{-1}$; $CoCl_2.6H_2O 0.10mgL^{-1}$; and $CuSO_4.5H_2O 0.19mgL^{-1}$.

It is preferred that the batch processes are carried out at temperatures between 23° C. and 37° C., ideally between 23° C. and 30° C. and optimally at 28° C. The batch processes are preferably commenced at a pH of between 4.5 and 8.0, ideally between 6.3 and 7.5 and optimally at 6.8.

The continuous processes of the invention are preferably carried out between 23° C. and 37° C., ideally at 28° C. They are preferably carried out at between pH 6.3 and 7.5, and ideally at 6.8. In these processes fresh culture medium is preferably added to give a dilution rate of between $0.01hr^{-1}$ and $0.5hr^{-1}$, most preferably between $0.04hr^{-1}$ and $0.1hr^{-1}$.

The culture media and culture conditions employed in process for producing the xenorhabdin compounds of the invention are also suitable for production of the other compounds of the invention having antibiotic and/or pesticidal activity.

The structure of the xenorhabdin compounds of the invention were elucidated by performing an x-ray diffraction analysis on a crystal of the xanthydrol derivative of one homologue, xenorhabdin I. Correlation of mass spectral, ultra violet, nuclear magnetic resonance and retention time data enabled structures to be assigned to the five homologues Xenorhabdin I-V and the acetate of Xenorhabdin II.

The following examples provide detailed descriptions of such procedures, together with a description of fractionation of the isolate and characterization of compounds of the invention.

EXAMPLE 1

A monoxenic culture of 1° form of *Xenorhadbus nematophilus* strain T319 (Enterobacteriaceae) was cultured on chicken offal as follows: medium (3 kg) of 12 parts of homogenised chicken offal to 1 part polyurethane foam was autoclaved in an evacuated polypropylene bag. The bag was inflated through tubes containing filters (0.45 m) with air. The inoculum was prepared by culturing the *X. nematophilus* in YS broth (500 mL) at 28° C. for 24 hours. The medium was inoculated and growth proceeded for 5 days.

The inoculated foam-homogenate mixture was steeped and manually mixed in ethanol (2×5 L) for 10 hours. The combined ethanolic extracts were concentrated by evaporation in vacuo at 40° C. then lyophilised to yield 143 g of extract. This extract (138 g) was stirred with ethyl acetate (4×500 mL) followed by acetone (2×500 mL), then the organic extracts were decanted, filtered, dried over anhydrous sodium sulfate and finally evaporated to yield a viscous, brown oil (50 g).

Fractionation of this oil was guided by an in vitro antibacterial bioassay. A solution of the sample was dissolved in DMSO then applied to a paper disc. This disc was placed on agar previously inoculated with *Micrococus luteus*. Zones of inhibition were measured after incubation at 37° C. for 20 hours.

The oil (50 g) was dissolved in petroleum ether (40°–60°, 150 mL) the Kieselgel 60 (35–70 mesh) (100 mL) was added and the solution evaporated. A dry sticky residue was recovered and it was applied to the top of a column (900×50 mm) of Kieselgel 60 (35–70 mesh, 1790 g) which was equilibrated in petroleum ether (40°–60°). The column was eluted sequentially as follows with the weight recovered indicated in the parentheses; pet. ether 4 L; pet. ether: ethyl acetate 9:1 2 L, 3:1 2 L (21.1 g); 2:1 4 L (7.7 g); 1:1 2 L (1.86 g); 1:2 4 L (2.65 g); ethyl acetate 2 L (92 g); methanol 4 L (9.64 g).

The yellow fraction eluted in petroleum ether:ethyl acetate 1:2 displayed antibacterial activity at an M.I.C. of 100 g.mL$^{-1}$.

The most active fraction (2.65 g) was triturated with petroleum ether 40°–60° (100 mL), filtered then dried to yield 555 mg of pale yellow solid.

A solution of this pale yellow solid (80 mg) in methanol (4 mL) was subjected to gel permeation chromatography on a column (88×3.0 cm, total volume 442 mL) of Sephadex LH-20 in methanol. The column eluate was pumped at 1 mL.min$^{-1}$ and monitored in a flow cell with a Uvicord SII (LKB) at 280 nm and fractionated with a Multirac (LKB). Two symmetrical u.v. absorbances were detected which corresponded to an inactive colourless crystalline solid at 331–373 mL (10 mg) and a crystalline yellow solid at 433–475 mL (57.8 mg). Several batches of sample were chromatographed to afford 265 mg of yellow solid.

This solid was subjected to preparative, isocratic, reverse phase HPLC on a Whatman Partisil-10 ODS column (10 m, 9.4×500 mm). The eluant (acetonitrile:water 1:1) was delivered at 4 mL.min$^{-1}$ with a Waters Model 6000A pump and the eluate monitored with a Waters Model 450 variable wavelength detector at 280 nm. Injection of 2–5 mg of sample in acetonitrile (200 L) were applied to the column. Three main constituents were detected and evaporation in vacuo followed by lyophilisation afforded three pure yellow, equiactive compounds, xenorhabdins I (42.7 mg), II (8.0 mg), and III (4.0 mg).

Xenorhabdin I: MP 192°–193° C.

$^{13}$C NMR (DMSO d6, 25 MHz) 13.98 (q), 21.93 (t), 24.86 (t), 30.88 (t), 34.69 (t), 110.74 (d), 115.42 (s), 133.62 (s), 134.09 (s), 167.96 (s), 171.91 (s) ppm.

$^1$H NMR (CD$_3$)$_2$CO 200 MHz reference acetone 2.04 ppm; 9.70 (0.37H broad); 8.74 (0.38H, broad); 6.98 (0.64H, sharp s); 3.22 (0.28H s); 2.93 (br s); 2.45 (2H, t, J=7.2 Hz); 1.64 (2H, br t of d); 1.32 (4H, m); 0.88 (3H, br d of t).

Signals at 9.70, 8.74, 2.93 ppm are exchangeable with CD$_3$OD.

IR (Nujol) cm$^{-1}$: 3250 (br), 1670, 1640, 1470.

Mass Spectrum, electron ionisation, m/z (%): 273 (0.6), 272 (5.6), 271 (7), M+270.0496 (55), C$_{11}$H$_{14}$N$_2$O$_2$S$_2$ requires 270.04982, 174(24), 173(26), 171.9759(100) C$_5$H$_4$N$_2$OS$_2$ requires 171.9766, 145(5), 143(7), 117(5), 101(5) 99(7), 72(5), 71(18), 57(8), 55(12), 45(15), 43(85).

Utraviolet spectrum (CH$_3$OH): 390 nm (max), 310 nm, 250 mn.

Xanthydrol Derivative

A solution of Xenorhabdin I (730 μg) in acetic acid (50 μL) was added to a solution of Xanthydrol (9-hydroxyxanthene) (3.3 mg) in acetic acid (50 μL). Crystals formed after standing overnight at room temperature. The mother liquor was syringed out and the crystals washed (2×50 μL) with cold acetic acid. They were recrystallised from a mixture of methanol (1 mL), acetic acid (50 μL), acetonitrile (50 μL) at 85°. The structure of these crystals was determined by x-ray diffraction.

Mass Spectrum electron ionisation m/z (%): 464(0.8), 182(22), 181(100), 172(23), 152(9), 86(6), 60(8), 45(9), 44(6), 43(11).

Xenorhabdin II: M.P. 210°–213° C.

$^1$H NMR (CD$_3$)$_2$CO 200 MHz reference acetone 2.04 ppm; 9.78 (0.14 H br); 6.96 (0.45H, s); 3.29 (0.47H, s); 2.86 small shoulder; 2.83 (3H s); 2.44 (2H, t J=7.4 Hz); 1.62 (3H, m); 1.25 (2H, d or t); 0.87 (6H, d J=6.5 Hz).

Signals at 9.78, 2.83 are exchangeable with CD$_3$OD.

Mass spectrum electron ionisation m/z (%): M+284 (2) C$_{12}$H$_{16}$N$_2$O$_2$S$_2$. 174(10), 173(13), 172(100), 143(3), 95(7), 69(60), 55(4), 45(5), 43(28). M+284.0659(20) C$_{12}$H$_{16}$N$_2$O$_2$S$_2$ requires 284.0653, 174(10), 173(13), 171.9771(100) C$_5$H$_4$N$_2$OS$_2$ requires 171.9766, 143(3), 95(7), 69(60), 55(4), 45(5), 43(28).

Ultraviolet spectrum (CH$_3$OH): 390 nm (max), 310 nm, 250 nm.

Xenorhabdin II Acetate

Pyridine (1 mL) was added to a solution of Xenorhabdin II (9.6 mg) in acetate anhydride (1 mL) and the solution left at room temperature for 50 hr. The solution was lyophilised, the residue was dissolved in acetonitrile (1 mL) then subjected to preparative isocrataic HLC in acetonitrile:water (3:2) on a Whatman Magnum 9 ODS column at 4 mL min$^{-1}$. An essentially quantitative yield of acetate was recovered.

Mass spectrum electron ionisation m/z (%): 328(5), 327 (7), 326.0760 C$_{14}$H$_{18}$N$_2$O$_3$S$_2$ requires 326.0759, 284 (19), 215(5), 214(39), 174(9), 173(11), 172(100), 171(8), 95(8), 69(9), 55(7), 43(35).

$^1$HNMR (CDCl$_3$) 200 mHz (CH$_3$)$_4$ Si reference: 8.08 (1H, sharp s, olefinic), 7.42 (1H, br s, N—H), 2.66 (3H, sharp s, CH$_3$CO), 2.36 (2H, t, J=7 Hz, CH$_2$—CO),1.7 (3H, br m, CH$_2$), 1.26 (2H, br m, CH$_2$), 0.91 (6H, d, J=7 Hz, geminal methyls).

Xenorhabdin III: M.P. 360° C.

$^1$NMR (CD$_3$)$_2$CO reference acetone 2.04 ppm; 9.7(m); 6.86(s); 3.27 (s); 2.86 (small shoulder); 2.83 (s); 2.44 (t, J=7.4 Hz); 1.64(m); 1.3(m); 0.86(m).

Mass spectrum electron ionisation m/z (%): 298.0815(32), C$_{13}$H$_{18}$N$_2$O$_2$S$_2$ requires 298.0810, 174(18), 173(20), 171.9769(100), C$_5$H$_4$N$_2$OS$_2$ requires 171.9766, 143(3), 127(3), 117(3), 101(3), 72(3), 57(32), 45(10), 43(26). Ultraviolet spectrum (CH$_3$OH): 390 nm (max), 310 nm, 250 nm.

Retention of the xenorhabdins I, II, IV, V and III on a Browlee RP-18 column (4.6×250 mm) pumped at 1.5 mL.min$^{-1}$ and detected at 405 nm were 4.6, 6.0, 6.64, 8.98 and 9.6 minutes respectively.

Xenorhabdin IV M.P. 165°

$^1$HNMR (CD$_3$)$_2$CO 200 MHz reference aetone 2.04 ppm; 8.85 (2.0H, broad s, NH); 7.08 (1H, sharp s, olefinic H); 3.28 (3H. sharp s, NMe); 2.43 (2H, t, J=7 Hz, CO—CH$_2$); 1.64 (2H, M, CH$_2$); 1.25 (4H, M, CH$_2$—CH$_2$); 0.85 (3H, M, CH$_3$).

Mass spectrum, electron ionisation, m/Z (%):286(3), 285(4), M+ 284.0654 (24) C$_{12}$H$_{16}$N$_2$O$_2$S$_2$ requires 248.0653; 189(1), 188(10), 187(11), 186(100), 185(5), 157(2), 130(1), 101(1), 99(1), 86(3), 71(3), 70(1), 69(1), 55(3), 45(3), 43(17), 42(7), 41(5).

Collision-Induced Dissociation Spectrum of M/z 186: 172(5), 171(35), 170(5), 169(81), 159(7), 158(29), 157(100), 156(5), 154(6), 153(42), 144(26), 143(48), 142(33), 141(20), 131(23), 130(42), 129(6), 128(6), 125(29), 124(8), 117(7), 116(29), 114(8), 113(15), 103(18), 102(33), 101(29), 100(15), 98(20), 87(11), 86(42), 85(14), 84(21), 82(16), 81(25), 72(43), 71(10), 70(11), 69(17), 68(5), 66(5), 65(8), 60(5), 57(6), 55(8), 53(6), 52(6), 45(24), 42(20).

Ultraviolet spectrum (CH$_3$OH) λ max 390 (ε=10000); 310 nm(ε=1000), 250 nm.

Infrared spectrum (K Br disc) cm$^{-1}$: 3260, 2920, 1680, 1650, 1610, 1540, 1440, 1240, 830 Xenorhabdin V 1HNMR (CD₃)₂CO 200 MHz reference acetone 2.04 ppm; 8.9 (m,NH); 7.10 (1H, sharp s, olefinic H); 3.29 (3H, sharp s, NMe); 2.42 1 (2H, t, J=7 Hz, CO—CH₂); 1.62 (3H, m,); 1.25 (2H, m); 0.87 (6H, d, J=6.5 Hz).

Mass Spectrum, electron ionisation, M/Z (%): 300(2), 299(4), 298.0807(20) $C_{13}H_{18}N_2O_2S_2$ requires 298.0810, 189(1), 188(10), 187(13), 186(100), 130(1), 101(1), 95(3), 86(3), 69(4), 57(3), 56(1), 55(5), 45(3), 44(1), 43(19), 42(7), 41(9). Ultraviolet spectrum (CH₃OH): 390 nm (max), 310 nm, 250 nm.

Fermentation techniques may be employed for large scale production of xenorhabdins, as will now be exemplified:

EXAMPLE 2

X. nematophilus strain T319 was grown in 3.5 liters of yeast extract-salts (YS) medium pH 6.7 which contained 5 g.L⁻¹ of yeast extract. A stirred laboratory fermenter was employed. It consisted of a 5 liter glass pipe section with stainless steel end plates. The stirrer, a flat blade turbine impeller was driven at 1425 rpm. Air was sparged into the fermenter at 0.5 vv⁻¹.min⁻¹, so that the dissolved oxygen concentration was maintained above 50% of air saturation. Chilled water was recirculated through an internal cooling coil and an on-off temperature controller was used to activate two 250 watt heating lamps to maintain the culture temperature at 28° C. A 3% v/v inoculum, which was grown for 20 hours in the yeast extract-salts medium in a shaker-incubator, at 28°, was used. The culture was grown in the fermenter for 48 hours before harvesting. A Beckman J2-21M centrifuge fitted with a continuous flow large pellet core (800 mL) rotor operating at 15,000 rpm (30,000×g), 15° C. was employed to harvest the cells. Sodium azide (600 mg) was added to the supernatant (3 liters) then it was pumped (9.7 mL. $min^{-1}$) through a column of Amberlite XAD-resin (34×2.5 cm). The resin was washed with water (2.5 liters). Evaporation of the methanolic fraction afforded a residue from which the xenorhabdins could be isolated by the chromatographic procedures outlined above.

EXAMPLE 3

Xenorhabdus nematophilus strain XQ-1 was grown in a continuous culture. Strain XQ1 was deposited with the ATCC on Nov. 2, 1983 and allocated number ATCC 39497. A Braun U-series fermenter with 5 L glass vessel was set up for a culture working volume of 2.3 L. Temperature was controlled at 28° C., and pH at 7.0 by automatic addition of 20% w/v phosphoric acid or 50% w/w sodium hydroxide as required. The level of dissolved oxygen was maintained at or above 40% of air saturation by manually adjusting air flow rate and stirrer speed.

Medium was prepared in 18 L batches containing the following ingredients: yeast extract 15 $g.L^{-1}$; sodium chloride 5 $g.L^{-1}$; ammonium sulfate 1 $g.L^{-1}$; magnesium sulfate 0.5 $g.L^{-1}$; potassium dihydrogen and dipotassium hydrogen orthophosphates each 1 $g.L^{-1}$. After sterilization by autoclaving, 2 L of this medium was introduced to the sterile fermenter and inoculated with 100 mL of an overnight culture of the primary form of XQ-1, in yeast extract-salts broth. This was allowed to grow batchwise for 8 hours, then fresh medium was pumped to the fermenter at a rate sufficient to give a dilution rate of 0.05 $hr^{-1}$. Thus one culture volume was collected in the reservoir via the culture off-take tube every 20 hours. Xenorhabdin production began within 24 hours and reached steady-state concentrations in the whole culture of 10.8 $mg.L^{-1}$ xenorhabdin I and 36.4 $mg.L^{-1}$ xenorhabdin II, giving a total productivity of some 2.4 $mg.L^{-1}.hr^{-1}$. Operation of the fermentation may be continued until equipment failure, productivity loss, or infection occurs. In this case significant reversion of the culture to the non-producing secondary form was observed after 140 hours when xenorhabdin productivity had fallen to 30% of the initial steady-state level, and 2° forms accounted for 31% of the viable cell population.

The growth, in agar, of the following organisms was found to be inhibited by the presence of an xenorhabdin compounds I, II, III, IV, or V according to this invention: Cellulomonas sp, *S. aureus, B. cereus subsp. mycoides, B. polymyxa, B. subtilis, E. coli, B. thuringiensis, Sh. sonnei, Serratia sp, Pr. vulgaris, Erw. carotovora, C. albicans and S. cerevisiae.*

It is to be understood that antibiotics according to this invention include the antibacterially active salts and other derivatives of the xenorhabdins. Moreover, the invention also embraces pharmaceutical compositions containing the antibiotics, as well as the use of the antibiotics in the treatment or prevention of disease.

The compounds of the invention may be administered orally, parentally or topically in dosage forms such as capsules, boluses, tablets, suppositories, solutions, suspensions, dispersions, powders, dusts, creams, and gels.

The formulations will contain at least one of the compounds of the invention and may contain other pharmaceutically active agents.

The formulations in solid form for oral administration such as tablets, capsules, pills, powders, granules and the like will usually be formulatd with finely divided diluents, fillers, disintegrating agents and/or binders such as starch, lactose, talc, magnesium stearate, vegetable gums and the like.

Liquid formulations for oral administration such as syrups, solutions, suspensions, elixirs and the like will usually be formulated with an aqueous base. Parenteral formulations will be, for example sterile solutions, suspensions or emulsions in water or organic solvents.

Topical formulations will include solutions, suspensions, ointments, micronised powders, aerosols and the like.

The formulations may be sterilised and/or may contain adjuvants such as preservatives, stabilizers wetting agents, emulsifiers, salts to vary osmotic pressure, or buffers.

In the pesticidal application of the invention, the compounds of the invention can be used alone or together with suitable carriers and/or diluents. The carriers or diluents can be solid or liquid, such as solvent, dispersing agents, wetting agents, binders, thickeners and extenders.

Pesticidal formulations are produced by conventional means such as mixing and/or grinding with suitable carriers or diluents.

Examples of solid preparations are wettable powders, dusts and granules. Examples of liquid preparations are solutions, water dispersible concentrates, emulsions or pastes.

We claim:

1. A process for the production of antibiotic xenorhabdin compounds of the formula:

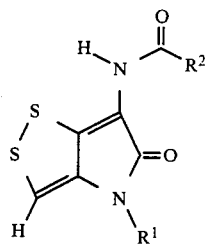

wherein $R^1$ is methyl, and $R^2$ is selected from the group consisting of n-pentyl and 4-methylpentyl, which process comprises culturing a xenorhabdin producing strain of *Xenorhabdus nematophilus* or *Xenorhabdus luminescens* in a culture medium in a fermenter having materials containing carbon and energy sources, nitrogen sources, inorganic nutrients, and a source of vitamins and growth factors in the presence of oxygen, maintaining the temperature of the culture medium between 23° C. and 37° C., maintaining the pH of the culture medium between 6.3 and 7.5 and continuously adding fresh culture medium and collecting culture medium from the fermenter to maintain the volume of said culture medium in the fermenter at a constant volume while adding fresh culture to maintain a dilution rate of between 0.01 $hr^{-1}$ and 0.5 $hr^{-1}$, and separating said compounds from the resultant culture broth.

2. The process of claim 1 wherein said xenorhabdin compound comprises 6-hexanoylamino-1,2-dithiolo[4,3-b]pyrrol-5-(4H)-one.

3. The process of claim 1 wherein said xenorhabdin compound comprises 6-(5-methylhexanoylamino)-1,2-dithiolo[4,3-b]pyrrol-5(1H)-one.

4. The process of claim 1 wherein said xenorhabdin compound comprises 6-octanoylamino-1,2-dithiolo[4,3-b]pyrrol-5(4H)-one.

5. The process of claim 1 wherein said xenorhabdin compound comprises 6-hexanoylamino-4-methyl-1,2-dithiolo[4,3-b]pyrrol-5(4H)-one.

6. The process of claim 1 wherein said xenorhabdin compound comprises 6-(3-methylpentanoylamino)-4-methyl-1,2-diothiolo[4,3-b]pyrrol-5(4H)-one.

7. The process of claim 1 wherein said pH is controlled at 6.8.

8. The process of claim 1 wherein said fresh culture medium is added to give a dilution of between 0.04 $hr^{-1}$ and 0.1 $hr^{-1}$.

* * * * *

UNITED STATES PATENT AND TRADEMARK OFFICE
CERTIFICATE OF CORRECTION

PATENT NO. : 4,672,130

DATED : June 9, 1987

INVENTOR(S) : Rhodes, et al.

It is certified that error appears in the above-identified patent and that said Letters Patent is hereby corrected as shown below:

Column 1, Line 9, "antibiotic" should be --antibiotics--.

Column 2, Line 42, "chromatorgraphy" should be --chromatography--.

Column 2, Line 55, "luminiscens" should be --luminescens--.

Column 4, Line 12, "process" should be --processes--.

Column 5, Line 25, "Injection" should be --Injections--.

Column 6, Line 2, "d or t" should be --d of t--.

Column 6, Line 18, "HLC" should be --HPLC--.

Column 6, Line 31, " 'NMR" should be --'H NMR--.

Column 6, Line 42, "Browlee" should be --Brownlee--.

Column 6, Line 46, "aetone" should be --acetone--.

Column 6, Line 47, "(2.OH," should be --(0.2H--.

UNITED STATES PATENT AND TRADEMARK OFFICE
CERTIFICATE OF CORRECTION

PATENT NO. : 4,672,130

DATED : June 9, 1987

INVENTOR(S) : Rhodes, et al.

Page 2 of 2

It is certified that error appears in the above-identified patent and that said Letters Patent is hereby corrected as shown below:

Column 6, Line 48, "(3H." should be --(3H,--.

Column 7, Line 3, "2.42I(2H" should be --2.42 (2H--.

Column 8, Line 56, "solvent" should be --solvents--.

Column 10, Line 9, "5(1H)-one." should be --5(4H)-one--.

Signed and Sealed this

Eleventh Day of October, 1988

*Attest:*

DONALD J. QUIGG

*Attesting Officer*     *Commissioner of Patents and Trademarks*